US011344570B2

(12) United States Patent
Ishikawa

(10) Patent No.: US 11,344,570 B2
(45) Date of Patent: May 31, 2022

(54) PENTOSAN POLYSULFATE AND MEDICINE CONTAINING PENTOSAN POLYSULFATE

(71) Applicant: OJI HOLDINGS CORPORATION, Tokyo (JP)

(72) Inventor: Suguru Ishikawa, Tokyo (JP)

(73) Assignee: OJI HOLDINGS CORPORATION, Tokyo (JP)

( * ) Notice: Subject to any disclaimer, the term of this patent is extended or adjusted under 35 U.S.C. 154(b) by 4 days.

(21) Appl. No.: 16/955,641

(22) PCT Filed: Dec. 18, 2018

(86) PCT No.: PCT/JP2018/046537
§ 371 (c)(1),
(2) Date: Jun. 18, 2020

(87) PCT Pub. No.: WO2019/124363
PCT Pub. Date: Jun. 27, 2019

(65) Prior Publication Data
US 2020/0384012 A1  Dec. 10, 2020

(30) Foreign Application Priority Data
Dec. 20, 2017 (JP) .............................. JP2017-244051

(51) Int. Cl.
*A61K 31/737* (2006.01)
*A61K 31/7004* (2006.01)
*A61K 9/00* (2006.01)

(52) U.S. Cl.
CPC ........ *A61K 31/737* (2013.01); *A61K 31/7004* (2013.01); *A61K 9/0019* (2013.01)

(58) Field of Classification Search
CPC .. A61P 19/00; A61P 13/10; A61P 9/00; A61P 29/00; A61P 43/00; A61P 37/106; A61P 37/08; A61K 31/7004; A61K 31/7024; A61K 31/737; A61K 9/06; A61K 9/08; C08B 37/00; C07H 11/00
USPC ............................................ 514/58; 536/122
See application file for complete search history.

(56) References Cited

U.S. PATENT DOCUMENTS

| 4,168,742 | A | | 9/1979 | Kluppel et al. |
| 4,699,900 | A | * | 10/1987 | Bayol ........................ A61P 3/06 514/54 |
| 4,713,373 | A | | 12/1987 | Bayol et al. |
| 4,727,063 | A | | 2/1988 | Naggi et al. |
| 5,516,765 | A | | 5/1996 | Andermann |
| 7,902,158 | B2 | | 3/2011 | Kuszmann et al. |
| 8,987,216 | B2 | | 3/2015 | Kuszmann et al. |
| 8,993,536 | B2 | | 3/2015 | Kakehi et al. |
| 2001/0005720 | A1 | | 6/2001 | Striker et al. |
| 2003/0109491 | A1 | | 6/2003 | Ulmer et al. |
| 2006/0194759 | A1 | | 8/2006 | Eidelson |
| 2007/0281893 | A1 | | 12/2007 | Kuszmann et al. |
| 2008/0249298 | A1 | | 10/2008 | Ulmer et al. |
| 2010/0055060 | A1 | | 3/2010 | Yoshida et al. |
| 2010/0261807 | A1 | * | 10/2010 | Laine ........................ C08L 5/14 523/122 |
| 2011/0118198 | A1 | | 5/2011 | Kuszmann et al. |
| 2011/0251154 | A1 | | 10/2011 | Stajic et al. |
| 2011/0281819 | A1 | | 11/2011 | Kakehi et al. |
| 2011/0306567 | A1 | | 12/2011 | Schofield et al. |
| 2020/0062867 | A1 | | 2/2020 | Ishikawa et al. |
| 2020/0146963 | A1 | | 5/2020 | Ishikawa et al. |

FOREIGN PATENT DOCUMENTS

| CA | 2018133 | A1 | 12/1990 |
| CN | 1051564 | A | 5/1991 |
| CN | 1832966 | A | 9/2006 |
| CN | 101014607 | A | 8/2007 |
| CN | 102061323 | A | 5/2011 |
| CN | 102300870 | A | 12/2011 |
| CN | 102766225 | A | 11/2012 |
| CN | 103320548 | A | 9/2013 |
| CN | 105907896 | A | 8/2016 |
| CN | 106832020 | A | 6/2017 |
| EP | 0 116 801 | B1 | 4/1987 |
| EP | 0889055 | A1 | 7/1999 |
| JP | S48-043100 | B1 | 12/1973 |
| JP | S60-063203 | A | 4/1985 |
| JP | S61-130301 | A | 6/1986 |
| JP | S61-130302 | A | 6/1986 |
| JP | S61-197601 | A | 9/1986 |

(Continued)

OTHER PUBLICATIONS

Trisha Gura, Science, Nov. 1997, 278(5340), 1041-42.*
The Merck Manual, 16th Ed., 1999, pp. 339-342 and 1488-1490.*
Smith et al, Journal of Inflammation, 2004, 1(3), pp. 1-12.*
Vergnolle, Mem. Inst. Oswaldo Cruz, Rio de Janeiro, 2005, 100 (suppl. 1), pp. 173-176.*
Douglas et al, MJA, 2006, 185(4), 228-233).*
"Technology of Wood Chemicals", CMC Publishing Co., Ltd., 2007, p. 108.

(Continued)

*Primary Examiner* — Ganapathy Krishnan
(74) *Attorney, Agent, or Firm* — Sughrue Mion, PLLC

(57) ABSTRACT

The present invention provides a pentosan polysulfate having a uronic acid content of 7.0 mass % to 15.0 mass % and an acetyl group content of 0 mass % to 2.0 mass %; a pharmaceutically acceptable salt thereof; or a pharmaceutically acceptable solvate of the pentosan polysulfate or of the pharmaceutically acceptable salt thereof. The pentosan polysulfate, the pharmaceutically acceptable salt thereof, or the pharmaceutically acceptable solvate of the pentosan polysulfate or of the pharmaceutically acceptable salt thereof are useful as an active ingredient of a medicament for preventing and/or treating a disease caused by abnormal enhancement of FGF-2 function, and as a pH buffer agent.

15 Claims, 2 Drawing Sheets

(56) References Cited

FOREIGN PATENT DOCUMENTS

| | | |
|---|---|---|
| JP | S62-004362 B2 | 1/1987 |
| JP | H03-20225 A | 1/1991 |
| JP | H09-509650 A | 9/1997 |
| JP | H10-195107 A | 7/1998 |
| JP | H11-049802 A | 2/1999 |
| JP | H11-180821 A | 7/1999 |
| JP | 2003-183303 A | 7/2003 |
| JP | 2003-221307 A | 8/2003 |
| JP | 2003-221339 A | 8/2003 |
| JP | 2004-513185 A | 4/2004 |
| JP | 2005-501931 A | 1/2005 |
| JP | 2009-196915 A | 9/2009 |
| JP | 2009-532467 A | 9/2009 |
| JP | 2013-177433 A | 9/2013 |
| JP | 2014-129383 A | 7/2014 |
| JP | 2015-038061 A | 2/2015 |
| JP | 2016-514090 A | 5/2016 |
| JP | 6225321 B1 | 11/2017 |
| JP | 6281659 B1 | 2/2018 |
| WO | 1991/016058 A1 | 10/1991 |
| WO | 1995/014491 A3 | 6/1995 |
| WO | 1995/014492 A2 | 6/1995 |
| WO | 1998/006409 A2 | 2/1998 |
| WO | 02/041901 A1 | 5/2002 |
| WO | 2005/014656 A1 | 2/2005 |
| WO | 2005/117912 A1 | 12/2005 |
| WO | 2007/014155 A2 | 2/2007 |
| WO | 2007/123800 | 11/2007 |
| WO | 2007/138263 A1 | 12/2007 |
| WO | 2008/107906 A1 | 9/2008 |
| WO | 2009/087581 A1 | 7/2009 |
| WO | 2010/000013 A1 | 1/2010 |
| WO | 2010/089617 A2 | 8/2010 |
| WO | 2010/089617 A3 | 8/2010 |
| WO | 2012/101544 A1 | 8/2012 |
| WO | 2012/114349 A1 | 8/2012 |
| WO | 2013/186857 A1 | 12/2013 |
| WO | 2014/114723 A1 | 7/2014 |
| WO | WO 2014/114723 A1 * 7/2014 ............. C08B 37/00 |
| WO | 2014/122251 A2 | 8/2014 |
| WO | 2014/122251 A3 | 8/2014 |
| WO | 2016/184887 A1 | 11/2016 |
| WO | 2016/191698 A1 | 12/2016 |
| WO | 2018/043667 A1 | 3/2018 |
| WO | 2018/043668 A1 | 3/2018 |

OTHER PUBLICATIONS

International Preliminary Report on Patentability for PCT/JP2018/007138 dated Oct. 24, 2018 corresponding to U.S. Appl. No. 16/489,074.
International Search Report for PCT/JP2018/007138 dated Mar. 27, 2018 corresponding to U.S. Appl. No. 16/489,074.
Ishihara et al., "Isolation of Xylan from Hardwood by Alkali Extraction and Steam Treatment", Mokuzai Gakkaishi, Journal of Wood Science 1996, vol. 42, No. 12, pp. 1211-1220 (11 pages total).
Kabel et al., "Hydrothermally treated xylan rich by-products yield different classes of xylo-oligosaccharides" Carbohydrate Polymers, 2002, vol. 50, No. 1, pp. 47-56.
Kabel et al., "Complex xylo-oligosaccharides identified from hydrothermally treated Eucalyptus wood and brewery's spent grain", Carbohydrate Polymers, 2002, vol. 50, No. 2, pp. 191-200.
Koutaniemi et al., "Distinct roles of carbohydrate esterase family CE16 acetyl esterases and polymer-acting acetyl xylan esterases in xylan deacetylation", Journal of Biotechnology, 2013, vol. 168, No. 4, pp. 684-692.
Pawar et al., "Acetylation of woody lignocellulose: significance and regulation", Frontiers in Plant Science, 2013, vol. 4, No. 118, pp. 1-8.
International Search Report for PCT/JP2017/031434 dated Oct. 31, 2017 corresponding to U.S. Appl. No. 16/643,265.
Office Action issued by the Japanese Patent Office dated Apr. 18, 2017 in JP Application No. 2017-040067.
Office Action issued by the Japanese Patent Office dated Oct. 3, 2017 in JP Application No. 2017-166559.
Moure et al., "Advances in the manufacture, purification and applications of xylo-oligosaccharides as food additives and nutraceuticals", Process Biochemistry, 2006, vol. 41, Issue 9, pp. 1913-1923.
Gullón et al., "Structural features and properties of soluble products derived from *Eucalyptus globulus* hemicelluloses", Food Chemistry, 2011, vol. 127, No. 4, p. 1798-1807.
Gullón et al., "Membrane processing of liquors from *Eucalyptus globulus* autohydrolysis", Journal of Food Engineering, 2008, vol. 87, No. 2, pp. 257-265.
Ishikawa et al., "Research and development of sulphated hemicellulose (PPS)", The 62nd Japan Technical Association of the Pulp and Paper Industry Annual Meeting, 2019, pp. 1-5.
Scully et al., "The antiheparin effect of a heparinoid, pentosane polysulphate", Biochem. J, 1984, vol. 218, pp. 657-665.
McCarty et al., "Sulfated glycosaminoglycans and glucosamine may synergize in promoting synovial hyaluronic acid synthesis", Medical Hypotheses, 2000, vol. 54, No. 5, pp. 798-802.
Ferrao et al., "The effect of heparin on cell proliferation and type-I collagen synthesis by adult human dermal fibroblasts", Biochimica et Biophysica Acta, 1993, vol. 1180, pp. 225-230.
International Search Report for PCT/JP2018/020644 dated Sep. 4, 2018, corresponding to U.S. Appl. No. 16/617,783.
International Search Report for PCT/JP2017/031433 dated Oct. 31, 2017 corresponding to the present application.
Office Action issued by the Japanese Patent Office dated Jan. 8, 2019 in JP Application No. 2018-553269.
Office Action issued by the Japanese Patent Office dated Feb. 5, 2019 in JP Application No. 2018-229611.
Hirst et al., "Water-soluble Polysaccharides of Cladophora" Journal of the Chemical Society, 1965, pp. 2958-2967.
International Search Report for PCT/JP2018/033535 dated Nov. 27, 2018, corresponding to U.S. Appl. No. 16/646,243.
International Search Report for PCT/JP2018/046537 dated Mar. 5, 2019.
International Search Report for PCT/JP2017/031432 dated Oct. 31, 2017.
Office Action issued by the Japanese Patent Office dated Jul. 17, 2019 in JP Application No. 2018-516078.
Office Action issued by the Japanese Patent Office dated Jul. 17, 2019 in JP Application No. 2018-516079.
González et al., "Demonstration of Inhibitory Effect of Oral Shark Cartilage on Basic Fibroblast Growth Factor-Induced Angiogenesis in the Rabbit Cornea", Biol. Pharm. Bull, 2001, vol. 24, No. 2, pp. 151-154.
Swain et al., "Heparin-Binding Growth Factor Blockade with Pentosan Polysulfate", Annals of the New York Academy of Sciences, 1993, vol. 698, pp. 63-70.
Zugmaier et al., "Polysulfated Heparinoids Selectively Inactivate Heparin-Binding Angiogenesis Factors", Annals of the New York Academy of Sciences, 1999, vol. 886, pp. 243-248.
Zugmaier et al., "Inhibition by Pentosan Polysulfate (PPS) of Heparin-Binding Growth Factors Released From Tumor Cells and Blockage by PPS of Tumor Growth in Animals", Journal of the National Cancer Institute, 1992, vol. 84, No. 22, pp. 1716-1724.
Garrote et al., "Non-isothermal autohydroiysis of *Eucalyptus* wood", Wood Science and Technology, 2002, vol. 36, pp. 111-123.
Sivová et al., "Fagus sylvatica glucuronoxylan sulfate-chemical profile and pharmacological view", Starch, 2015, vol. 68, pp. 621-628.
Rhee et al., "Engineering the Xylan Utilization System in Bacillus subtilis for Production of Acidic Xylooligosaccharides", Applied and Environmental Microbiology, 2014, vol. 80, No. 3, pp. 917-927.
Maekawa et al., "Infrared Spectra of Wood Cellulose and Related Polysaccharide", Kyoto University, Research Institute Report, 1968, vol. 43, pp. 1-8.
Kabel et al., "In Vitro Fermentability of Differently Substituted Xylo-oligosaccharides", Journal of Agricultural and Food Chemistry, 2002, vol. 50, pp. 6205-6210.
Office Action issued by Japanese Patent Office dated Oct. 9, 2018 in JP Application No. 2018-516078.

(56) References Cited

OTHER PUBLICATIONS

International Preliminary Report on Patentability dated Dec. 3, 2019 from the International Bureau in International Application No. PCT/JP2018/020644, corresponding to U.S. Appl. No. 16/617,783.
Extended European Search Report dated Feb. 3, 2021, from the European Patent Office in EP application No. 18809395.9, corresponding to U.S. Appl. No. 16/617,783.
Takayuki Ohbuchi et al., "Structural Analysis of Neutral and Acidic Xylooligosaccharides from Hardwood Kraft Pulp, and Their Utilization by Intestinal Bacteria in Vitro", Bioscience, Biotechnology, and Biochemistry, vol. 73, No. 9, 2009, pp. 2070-2076 ( 8 pages total).
Office Action dated Jun. 2, 2021, from the U.S. Patent and Trademark Office in U.S. Appl. No. 16/643,215.
Office Action dated Mar. 2, 2021 in U.S. Appl. No. 16/489,074.
Elmiron®-100 MG (Pentosan Polysulfate Sodium) Capsules, 2002, https://www.accessdata.fda.gov/drugsatfda_docs/label/2020/020193s014lbl.pdf (14 pages).
Office Action dated Mar. 25, 2021 issued by the Indian Patent Office in Indian Application No. 201947036653.
Stephan Daus et al., "Homogeneous Sulfation of Xylan from Different Sources", Macromolecular Materials and Engineering, 2011, vol. 296,pp. 551-561 (11 pages).
Office Action dated Apr. 27, 2021 in U.S. Appl. No. 16/646,243.
Office Action dated Nov. 16, 2020 in Australian Application No. 2018276567.
Stephen Dealler et al., "Pentosan polysulfate as a prophylactic and therapeutic agent against prion disease", IDrugs, vol. 6, No. 5, Jun. 1, 2003, pp. 470-478, XP055777416 (10 pages total).
Extended European Search Report dated Feb. 26, 2021 from the European Patent Office in EP Application No. 17846672.8, corresponding to U.S. Appl. No. 16/643,265.
Office Action dated Oct. 25, 2021 issued by China National Intellectual Property Administration in Chinese Patent Application No. 201880058953.X, which corresponds to U.S. Appl. No. 16/646,243.
Teleman et al., "Characterization of O-acetyl-(4-O-methylglucurono)xylan isolated from birch and beech", Carbohydrate Research, 2002, vol. 337, pp. 373-377 (5 pages total).
Office Action dated Sep. 17, 2021 by Indian Patent Office in Indian Application No. 202047012044.
Office Action dated Aug. 30, 2021 by China National Intellectual Property Administration in Chinese Application No. 201780094371. 2.
Mi et al., "Preparation of corn stover pentosan sulfate", Journal of Changchun University of Technology (Natural Science Edition), 2014, vol. 35, No. 6, pp. 716-719 (4 pages total).
Office Action dated Jan. 4, 2022 from the Indian Patent Office for the corresponding IN patent application No. 202047029636.
Extended European Search Report dated Sep. 29, 2021 by European Patent Office in European Application No. 18890627.5.
Herbert et al., "Activity of Pentosan Polysulphate and Derived Compounds on Vascular Endothelial Cell Proliferation and Migration Induced by Acidic and Basic FGF In Vitro", Biochemical Pharmacology, 1988, vol. 37, No. 22, pp. 4281-4288 (8 pages total).
U.S. Appl. No. 16/617,783, filed Nov. 27, 2019, Kotaro Ishikawa et al.
U.S. Appl. No. 16/489,074, filed Aug. 27, 2019, Kotaro Ishikawa et al.
U.S. Appl. No. 16/643,265, filed Feb. 28, 2020, Kotaro Ishikawa et al.
U.S. Appl. No. 16/643,215, filed Feb. 28, 2020, Kotaro Ishikawa et al.
U.S. Appl. No. 16/646,243, filed Mar. 11, 2020, Kotaro Ishikawa et al.

* cited by examiner

PENTOSAN POLYSULFATE AND MEDICINE CONTAINING PENTOSAN POLYSULFATE

CROSS REFERENCE TO RELATED APPLICATIONS

This application is a National Stage of International Application No. PCT/JP2018/046537 filed Dec. 18, 2018, claiming priority based on Japanese Patent Application No. 2017-244051, filed Dec. 20, 2017.

TECHNICAL FIELD

The present invention relates to a pentosan polysulfate, and a medicament comprising the pentosan polysulfate.

BACKGROUND ART

A basic fibroblast growth factor (FGF-2 or b-FGF) is known to be involved in diseases associated with abnormal angiogenesis, such as tumors and arthritis (Patent Literature (PTL) 1). FGF-2 is a heparin-binding growth factor that binds to the FGF-2 receptor of cells by binding to heparan sulfate.

Pentosan polysulfate is known as one of the substances that inactivate FGF-2. Pentosan polysulfate has been reported to inhibit angiogenesis etc. (Non-Patent Literature (NPL) 1 to Non-Patent Literature (NPL) 3). Pentosan polysulfate is considered to bind to FGF-2, and thereby inhibit FGF-2 from binding to heparan sulfate.

Pentosan polysulfate has also been reported to actually inhibit the growth of tumors (Patent Literature (PTL) 2 and Non-Patent Literature (NPL) 4).

Pentosan polysulfate is produced by chemical sulfation of xylan obtained from hardwood (e.g., beech). Pentosan polysulfate is composed of a sulfated linear polysaccharide in which β-D-xylopyranose is linearly bonded; and has 4-O-methylglucuronic acid, i.e., uronic acid, per roughly every 10 xylopyranose units (Patent Literature (PTL) 3 and Patent Literature (PTL) 4). Patent Literature (PTL) 5 discloses that pentosan polysulfate having a uronic acid content of 4.3 to 6% was obtained by a method comprising fractionating commercially available pentosan polysulfate (SP-54) to obtain a low-molecular-weight pentosan polysulfate.

CITATION LIST

Patent Literature

PTL 1: WO2013/186857
PTL 2: JPH3-20225A
PTL 3: WO2010/000013
PTL 4: JP2009-532467A
PTL 5: JPS61-197601A

Non-Patent Literature

NPL 1: Gonzalez et al., Biol. Pharm. Bull., 2001; 24; 2; 151-154
NPL 2: S. Swain et al., Annals of the New York Academy of Sciences, 1993; 698; 63-67
NPL 3: G. Zugmaier et al., Annals of the New York Academy of Sciences, 1999; 886; 243-248
NPL 4: G. Zugmaier et al., Journal of the National Cancer Institute, 1992; 84; 22; 1716-1724

SUMMARY OF INVENTION

Technical Problem

An object of the present invention is to provide a novel pentosan polysulfate that has an activity preferable for pharmaceutical application, or application as a pH buffer agent.

Means for Solving the Problem

As a result of intensive study to solve the above problem, the present inventors found a novel pentosan polysulfate that has a high inhibitory activity to inhibit the binding between FGF-2 and heparan sulfate, compared with conventional pentosan polysulfate. The inventors further found that this pentosan polysulfate can also function as a pH buffer agent. The present invention has been accomplished based on these findings.

Specifically, the present invention provides the following [1] to [13].

[1] A pentosan polysulfate having a uronic acid content of 7.0 mass % to 15.0 mass %, and an acetyl group content of 0 mass % to 2.0 mass %;

a pharmaceutically acceptable salt thereof; or a pharmaceutically acceptable solvate of the pentosan polysulfate or of the pharmaceutically acceptable salt thereof.

[2] The pentosan polysulfate according to [1], wherein the pentosan polysulfate has a uronic acid content of 7.5 mass % to 13.0 mass %;

a pharmaceutically acceptable salt thereof; or a pharmaceutically acceptable solvate of the pentosan polysulfate or of the pharmaceutically acceptable salt thereof.

[3] The pentosan polysulfate according to [1] or [2], wherein the pentosan polysulfate has a weight average molecular weight of 5000 or less;

a pharmaceutically acceptable salt thereof; or a pharmaceutically acceptable solvate of the pentosan polysulfate or of the pharmaceutically acceptable salt thereof.

[4] The pentosan polysulfate according to [3], wherein the pentosan polysulfate has an acetyl group content of 0 to 0.3 mass %;

a pharmaceutically acceptable salt thereof; or a pharmaceutically acceptable solvate of the pentosan polysulfate or of the pharmaceutically acceptable salt thereof.

[5] The pentosan polysulfate according to any one of [1] to [4], wherein the pentosan polysulfate has a structure represented by Formula II:

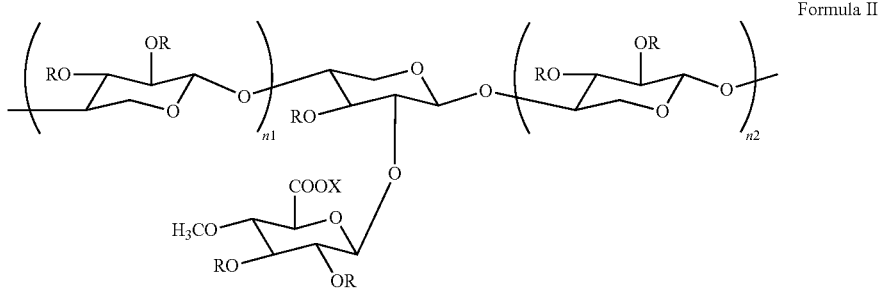

Formula II wherein R each independently represents a hydrogen atom, —COCH$_3$, or —SO$_3$X$^1$, and at least one R in the molecule is —SO$_3$X$^1$, wherein X$^1$ represents a hydrogen atom or a monovalent or divalent metal; X represents a hydrogen atom or a monovalent or divalent metal; and n1 and n2 each independently represent an integer of 0 or more and 30 or less, and at least one of n1 and n2 is an integer of 1 or more;
a pharmaceutically acceptable salt thereof; or
a pharmaceutically acceptable solvate of the pentosan polysulfate or of the pharmaceutically acceptable salt thereof.

[6] The pentosan polysulfate according to [5], wherein each R independently represents a hydrogen atom or —SO$_3$X;
a pharmaceutically acceptable salt thereof; or
a pharmaceutically acceptable solvate of the pentosan polysulfate or of the pharmaceutically acceptable salt thereof.

[7] The pentosan polysulfate according to [5] or [6], wherein X is sodium;
a pharmaceutically acceptable salt thereof; or
a pharmaceutically acceptable solvate of the pentosan polysulfate or of the pharmaceutically acceptable salt thereof.

[8] A medicament comprising as an active ingredient the pentosan polysulfate according to any one of [1] to [7];
a pharmaceutically acceptable salt thereof; or
a pharmaceutically acceptable solvate of the pentosan polysulfate or of the pharmaceutically acceptable salt thereof.

[9] The medicament according to [8], which is for use in the prevention and/or treatment of a disease caused by abnormal enhancement of FGF-2 function.

[10] The medicament according to [9], wherein the disease caused by abnormal enhancement of FGF-2 function is cancer, autoimmune disease, allergic disease, inflammatory disease, cardiac dysplasia, vascular dysplasia, or skeletal dysplasia.

[11] The medicament according to claim 9, which is for use in the prevention and/or treatment of cystitis or arthritis.

[12] The medicament according to any one of [8] to [11], which is an injectable formulation.

[13] A pH buffer agent comprising the pentosan polysulfate according to any one of [1] to [7];
a pharmaceutically acceptable salt thereof; or
a pharmaceutically acceptable solvate of the pentosan polysulfate or of a pharmaceutically acceptable salt thereof.

From another point of view, the present invention provides:
a method for preventing and/or treating a disease caused by abnormal enhancement of FGF-2 function, comprising administering an effective amount of the pentosan polysulfate according to any one of [1] to [7], a pharmaceutically acceptable salt thereof, or a pharmaceutically acceptable solvate of the pentosan polysulfate or of a pharmaceutically acceptable salt thereof to a human or an animal;

use of the pentosan polysulfate according to any one of [1] to [7], a pharmaceutically acceptable salt thereof, or a pharmaceutically acceptable solvate of the pentosan polysulfate, or of a pharmaceutically acceptable salt thereof, for producing a medicament for preventing and/or treating a disease caused by abnormal enhancement of FGF-2 function;

use of the pentosan polysulfate according to any one of [1] to [7], a pharmaceutically acceptable salt thereof, or a pharmaceutically acceptable solvate of the pentosan polysulfate, or of a pharmaceutically acceptable salt thereof, for preventing and/or treating a disease caused by abnormal enhancement of FGF-2 function; and the pentosan polysulfate according to any one of [1] to [7], a pharmaceutically acceptable salt thereof, or a pharmaceutically acceptable solvate of the pentosan polysulfate or of a pharmaceutically acceptable salt thereof, for use as a medicament for preventing and/or treating a disease caused by abnormal enhancement of FGF-2 function.

Advantageous Effects of Invention

The present invention provides a pentosan polysulfate that has a high inhibitory activity to inhibit the binding between FGF-2 and heparan sulfate. The pentosan polysulfate of the present invention is useful as a medicament for preventing and/or treating a disease caused by abnormal enhancement of FGF-2 function, such as cancer or arthritis. Further, the pentosan polysulfate of the present invention can also be used as a pH buffer agent.

DESCRIPTION OF EMBODIMENTS

Figure 1:
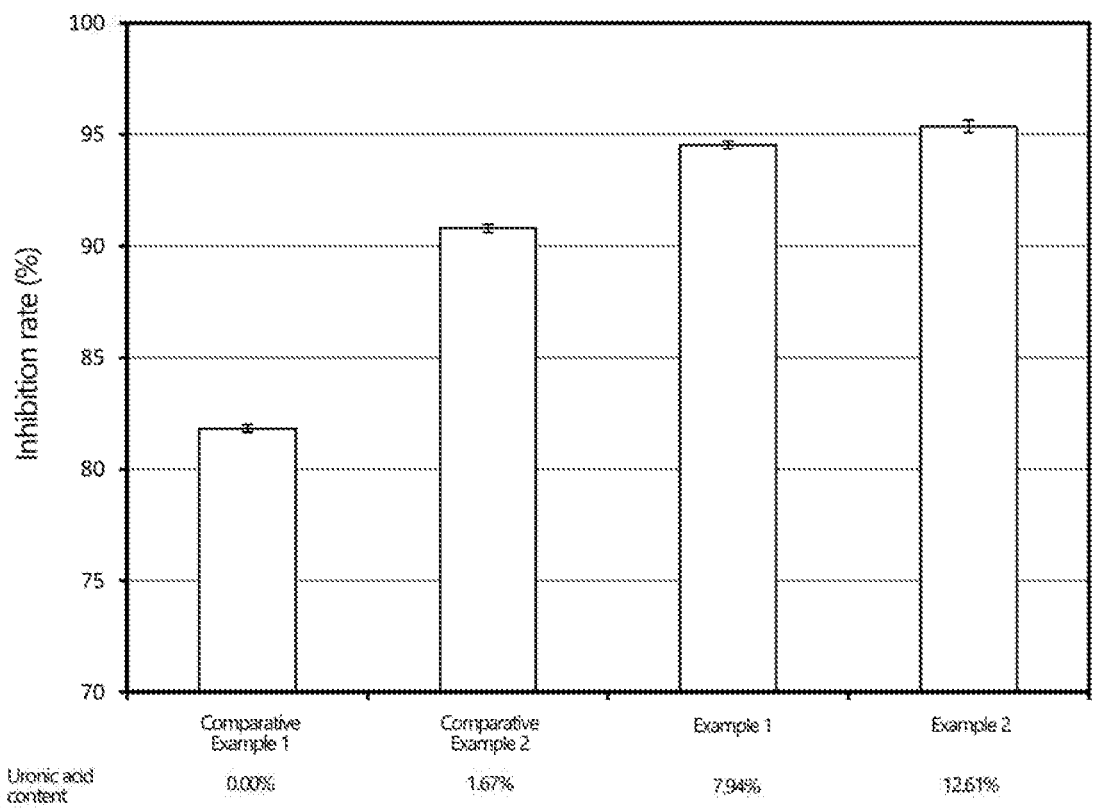
FIG. 1 is a graph showing the effect of the uronic acid content of pentosan polysulfate on inhibitory activity to inhibit the binding between FGF-2 and heparan sulfate.

The present invention is described below in detail. The constituent features may be described below based on typical embodiments and specific examples; however, the present invention is not limited to such embodiments.

In the present specification, "comprising . . . as an active ingredient" means containing as a main active ingredient, and containing in such an amount that an effect is exhibited.

The phrase "prevention and/or treatment" means "prevention," "treatment," or "prevention and treatment." For example, the "medicament for preventing and/or treating" may only function as a prophylactic agent, or as a therapeutic agent; or may have functions as both a prophylactic agent and a therapeutic agent.

Pentosan Polysulfate

Pentosan polysulfate is a compound obtained by sulfation of at least one hydroxyl group of xylooligosaccharide. In the present specification, pentosan polysulfate includes salts of pentosan polysulfate, solvates of pentosan polysulfate, and solvates of salts of pentosan polysulfate. Salts of pentosan polysulfate are preferably pharmaceutically acceptable salts, and examples include pentosan polysulfate sodium, pentosan polysulfate potassium, pentosan polysulfate calcium, and the like. The solvates are preferably pharmaceutically acceptable solvates. Examples of solvents include water.

Pentosan polysulfate has a structure represented by Formula II. Pentosan polysulfate may contain one structure represented by Formula II, or may contain two or more structures represented by Formula II. When pentosan polysulfate contains two or more structures represented by Formula II, the structure represented by Formula II is a structure representing a repeating unit of pentosan polysulfate.

of Formula II. In Formula II, $R^{1X}$ is a hydrogen atom or —$SO_3X^1$; $X^1$ is a hydrogen atom or a monovalent or divalent metal; and $X^1$ is preferably a hydrogen atom, sodium, potassium, or calcium, more preferably sodium, potassium, or calcium, and particularly preferably sodium.

In the above formula, X is preferably a monovalent or divalent metal. A pharmaceutically acceptable salt of pentosan polysulfate is preferable. For example, X is preferably sodium, potassium or calcium. In this case, the salt of pentosan polysulfate is pentosan polysulfate sodium, pentosan polysulfate potassium, or pentosan polysulfate calcium. Among these, the salt of pentosan polysulfate is particularly preferably pentosan polysulfate sodium.

The pentosan polysulfate of the present invention has a uronic acid content of 7.0 mass % to 15.0 mass %. The pentosan polysulfate of the present invention preferably has a uronic acid content of 7.5 mass % to 14.0 mass %, and more preferably 7.7 mass % to 13.0 mass %. The above proportion does not have to be met by a single molecule, but may be satisfied by pentosan polysulfate as an entire mixture of individual molecules.

The pentosan polysulfate of the present invention may be a mixture of molecules represented by Formula II that are different from each other in the n1 and n2 values, the kind of substituent R, and/or the degree of substitution.

Pentosan polysulfate has a structure obtained by sulfating a xylooligosaccharide. The pentosan polysulfate of the present invention is preferably obtained by sulfating an acidic xylooligosaccharide. Among xylooligosaccharides having the structure obtained by sulfating a xylooligosaccharide,

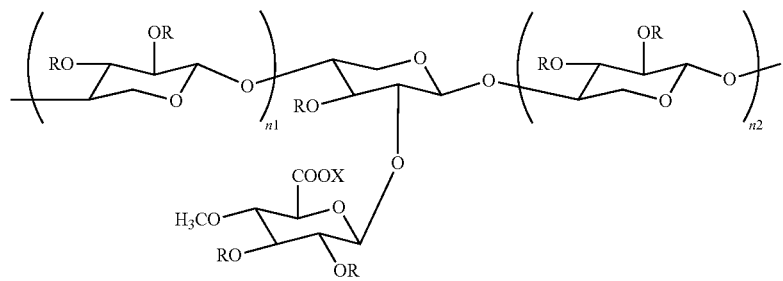

Formula II

In Formula II, R each independently represents a hydrogen atom, —$COCH_3$, or —$SO_3X^1$, and at least one R in the molecule is —$SO_3X^1$, wherein $X^1$ represents a hydrogen atom or a monovalent or divalent metal, and $X^1$ is preferably a hydrogen atom, sodium, potassium, or calcium, more preferably sodium, potassium, or calcium, and particularly preferably sodium; X is a hydrogen atom or a monovalent or divalent metal, and X is preferably sodium, potassium, or calcium, and is particularly preferably sodium; and n1 and n2 each independently represent an integer of 0 or more and 12 or less, and at least one of n1 and n2 is an integer of 1 or more.

In Formula II, n1+n2 is preferably from 1 to 10, more preferably from 2 to 8, and even more preferably from 3 to 6.

The portion that is an end of the structure represented by Formula II and that does not bind to a structure represented by Formula II may be —OR. That is, —OR may bind to the left terminus (n1 side) of Formula II, whereas —R may bind to the right terminus (n2 side) of Formula II. It is particularly preferable that —$OR^{1X}$ binds to the left terminus (n1 side) of Formula II, and —$R^{1X}$ binds to the right terminus (n2 side)

neutral xylooligosaccharides are xylooligosaccharides that do not contain uronic acid. Acidic xylooligosaccharides are xylooligosaccharides in which at least one uronic acid is bound to at least one of the xylose units in a xylooligosaccharide molecule. That is, acidic xylooligosaccharides have at least one uronic acid residue as a side chain per xylooligosaccharide molecule. The number of uronic acid residues contained per xylooligosaccharide molecule can be measured by the carbazole-sulfuric acid method, or the colorimetric method using sodium tetraborate. The uronic acid content (mass %) of pentosan polysulfate refers to a value calculated from the number of uronic acid residues in a predetermined amount of pentosan polysulfate obtained by the carbazole-sulfuric acid method, as described in the Examples.

The sulfur content of the pentosan polysulfate of the present invention is preferably 10.0 mass % or more, more preferably 12.0 mass % or more, even more preferably 15.5 mass % or more, and particularly preferably 16.5 mass % or more. The sulfur content of the pentosan polysulfate is preferably 20.0 mass % or less. Here, the sulfur content of pentosan polysulfate is a value determined according to the oxygen flask combustion method described in the Japanese Pharmacopoeia.

Known pentosan polysulfate is considered to contain a certain amount of xylose units to which one or more acetyl groups (—COCH$_3$) are bonded together with uronic acid residues (see, for example, WO2014/114723). In contrast, the pentosan polysulfate of the present invention preferably has an acetyl group content of 0 to 2.0 mass %, more preferably 0 to 1.0 mass %, even more preferably 0 to 0.4 mass %, still even more preferably 0 to 0.3 mass %, and particularly preferably substantially 0 mass %. In order to obtain pentosan polysulfate having an acetyl group content of 0 to 2.0% by mass, the pentosan polysulfate of the present invention is preferably produced through a deacetylation step described below.

The acetyl group content of polysulfate pentosan can be calculated from the integral ratio of peaks in H-NMR measurement. Specifically, first, $^1$H-NMR measurement is performed using a $^1$H-NMR measurement solution containing a specific amount of pentosan polysulfate and a specific amount of an internal standard substance. By comparing the peak for acetyl group to the peak for a specific group of the internal standard substance in the obtained spectrum to obtain an integral ratio thereof, the molar amount of acetyl groups in the solution is obtained. The molar amount of acetyl groups is then multiplied by 43; and the obtained value is divided by the average molecular weight obtained separately, so as to obtain the mass % of acetyl groups.

The weight average molecular weight (Mw) of the pentosan polysulfate of the present invention is not particularly limited; and may be, for example, 5000 or less, 4000 or less, 3900 or less, or 3800 or less, or 3750 or less. In this case, the lower limit of the weight average molecular weight (Mw) of the pentosan polysulfate is preferably 1000.

The number average molecular weight (Mn) of the pentosan polysulfate is not particularly limited; and may be, for example, 5000 or less, 4000 or less, 3900 or less, 3800 or less, or 3750 or less. In this case, the lower limit of the number average molecular weight (Mn) of the pentosan polysulfate is preferably 300.

The weight average molecular weight (Mw) and the number average molecular weight (Mn) of the pentosan polysulfate of the present invention can be measured by GPC (gel permeation chromatography). As the GPC column, a YMC-Pack Diol-300 and YMC-Pack Diol-60 (both manufactured by YMC) connected to each other can be used. The GPC conditions can be, for example, the following conditions.

Eluent: 25 mM potassium dihydrogen phosphate/25 mM dipotassium hydrogen phosphate/50 mM potassium chloride
Flow rate: 0.7 mL/min
Measurement temperature: 40° C.
Detector: refractive index detector The dispersion degree of the pentosan polysulfate is preferably 1.00 or more and 1.6 or less, more preferably 1.00 or more and 1.5 or less. The dispersion degree of the pentosan polysulfate is also preferably 1.00 or more and 1.4 or less. The degree of dispersion (D) of the pentosan polysulfate is calculated by the following formula.

Degree of dispersion ($D$)=eight average molecular weight (Mw)/Number average molecular weight (Mn)

The pentosan polysulfate obtained by the production method of the present invention described below has high purity, and tends to have a narrow molecular weight distribution. The pentosan polysulfate obtained by the production method of the present invention has excellent quality stability.

Application of Pentosan Polysulfate: Medicament

The pentosan polysulfate of the present invention can be used for applications, such as components of medicaments, foods, cosmetics, and other compositions.

The pentosan polysulfate of the present invention is particularly useful as an active ingredient of a medicament.

Examples of medicaments include medicaments for preventing and/or treating a disease caused by abnormal enhancement of FGF-2 function.

FGF-2 (basic fibroblast growth factor) is one of the growth factors, and is secreted from various cells. FGF-2 is deeply involved in cell proliferation and differentiation in developmental stages, and exhibits high expression during tissue repair in vivo. Further, FGF-2 is involved in abnormal angiogenesis, and has potent growth and migration-promoting effects on vascular endothelial cells. FGF-2, which has these functions, is known to be involved in diseases, such as tumors. It has also been clarified that FGF-2, which promotes angiogenesis and bone destruction, is a key molecule involved in pathology in chronic rheumatoid arthritis. Particularly high serum FGF-2 concentration in tumor with many blood vessels, such as kidney cancer, has been reported. FGF-2 is also present in various other tumors, such as prostate cancer, breast cancer, and lung cancer.

FGF-2 binds to an FGF receptor (FGFR), which induces the expression of various cytokines and receptor genes. FGF-2 has a heparin binding region, and binds to heparin and heparan sulfate. It is considered that when binding to FGFR, FGF-2 secreted from a cell is first bound to a heparan sulfate of an extracellular matrix, concentrated, and protected from protease. Therefore, the activity of inhibiting binding between FGF-2 and heparan sulfate can be an index for determining the effect of preventing and/or treating a disease caused by abnormal enhancement of FGF-2 function.

As shown in the Examples, pentosan polysulfate has an activity of inhibiting binding between FGF-2 and heparan sulfate; and this inhibitory activity is high when pentosan polysulfate has a uronic acid content of 7.0 to 15.0 mass %, and an acetyl group content of 0 to 2.0 mass %. Therefore, the pentosan polysulfate of the present invention is particularly useful for preventing and/or treating diseases caused by abnormal enhancement of FGF-2 function.

Specific examples of abnormal enhancement of FGF-2 function include abnormal angiogenesis by FGF-2. The abnormal enhancement of FGF-2 function can be determined, for example, by using an increase in serum FGF-2 concentration as an index.

Specific examples of diseases caused by abnormal enhancement of FGF-2 function include tumors, chronic inflammation such as arthritis, autoimmune diseases, allergic diseases, inflammatory diseases such as cystitis, cardiac dysplasia, vascular dysplasia, skeletal dysplasia, psoriasis, age-related macular degeneration, periodontal disease, scleroderma, neovascular glaucoma, and the like.

The pentosan polysulfate of the present invention is also useful as an active ingredient of a medicament for preventing and/or treating cystitis, particularly interstitial cystitis.

The dosage form of the medicament of the present invention is not particularly limited, and the medicament can be administered orally or parenterally. Preferably, the medicament may be parenterally administered by intravenous injection or infusion.

The medicament of the present invention may consist only of pentosan polysulfate, which is an active ingredient. Preferably, however, one or more appropriate pharmacologically and pharmaceutically acceptable additives may be added to pentosan polysulfate to provide a medicament in a form well known to persons skilled in the art.

Examples of pharmaceutically and pharmaceutically acceptable additives include excipients, disintegrants or disintegration aids, binders, lubricants, coating agents, pigments, diluents, bases, solubilizers or dissolution aids, isotonizing agents, buffers, pH adjusters, stabilizers, propellants, adhesives, and the like.

Examples of pharmaceutical preparations suitable for oral administration include tablets, capsules, powders, fine granules, granules, liquids, syrups, and the like. Examples of formulations for parenteral administration include injectable formulations, drip infusions, suppositories, inhalants, patches, and the like. To prepare formulations suitable for oral administration, transdermal administration, or transmucosal administration, for example, the following pharmacologically and pharmaceutically acceptable additives may be added. Examples of additives include excipients such as glucose, lactose, D-mannitol, starch, and crystalline cellulose; disintegrants or disintegration aids such as carboxymethylcellulose, starch, and calcium carboxymethylcellulose; binders such as hydroxypropylcellulose, hydroxypropylmethylcellulose, polyvinylpyrrolidone, and gelatin; lubricants such as magnesium stearate and talc; coating agents such as hydroxypropylmethylcellulose, sucrose, polyethylene glycol, and titanium oxide; and bases such as petrolatum, liquid paraffin, polyethylene glycol, gelatin, kaolin, glycerin, purified water, and hard fat. Other examples include propellants such as chlorofluorocarbon, diethyl ether, and compressed gas; adhesives such as sodium polyacrylate, polyvinyl alcohol, methylcellulose, polyisobutylene, and polybutene; and base cloth such as cotton cloth and plastic sheet. Pharmaceutical preparations can be formed by using such additives for pharmaceutical preparations.

To prepare pharmaceutical preparations suitable for injection or infusion, for example, the following additives for pharmaceutical preparations can be added. Examples of usable additives include solubilizing agents or solubilizing aids that can form aqueous or ready-to-use injectable formulations, such as distilled water for injection, saline, and propylene glycol; isotonizing agents such as glucose, sodium chloride, D-mannitol, and glycerin; buffers such as phosphates (e.g., disodium hydrogen phosphate and sodium dihydrogen phosphate), citrate, and acetate; and pH regulators such as inorganic acids, organic acids, inorganic bases, and organic bases.

As described later, the pentosan polysulfate of the present invention has a higher pH buffering capacity than pentosan polysulfate having a lower uronic acid content. Therefore, when the pH needs to be adjusted, for example, when the pentosan polysulfate of the present invention is to be provided in the form of a liquid preparation, an injectable formulation, a drip infusion, or the like, it is unnecessary to use a pH adjuster, or the amount of pH adjuster used can be reduced.

The dose of the medicament of the present invention is not particularly limited, and can be appropriately selected according to the administration form; the age, severity of disease, symptoms, and body weight of the patient; and other conditions. For example, when administered intravenously, subcutaneously, or intramuscularly, the medicament can be administered in an amount of 0.1 to 20 mg/kg, preferably 0.2 to 10 mg/kg, per day for an adult, in terms of the active ingredient.

Use of Pentosan Polysulfate: Anticoagulant

The pentosan polysulfate of the present invention can be used as an active ingredient of an anticoagulant.

Anticoagulants containing the pentosan polysulfate of the present invention can be provided not only as medicaments, but also as surface treatment agents for medical devices or medical materials. For example, such anticoagulants can be used as surface treatment agents for implantable artificial organs, artificial blood vessels, catheters, stents, blood bags, contact lenses, intraocular lenses, and surgical auxiliary instruments. Examples of methods for immobilizing the pharmaceutical composition on the surface of a medical device or a medical material include a method comprising bringing the pharmaceutical composition into contact with the medical device or the medical material, and irradiating the contact portion with radiation.

Use of Pentosan Polysulfate: pH Buffer

As shown in the Examples, the pentosan polysulfate of the present invention has a higher pH buffering capacity than the pentosan polysulfate having a lower uronic acid content. Therefore, the pentosan polysulfate of the invention can be used as a pH buffer agent. The pentosan polysulfate of the present invention exhibits buffering action to maintain the pH in the range of pH 4 to pH 6. For example, an injectable formulation having a pH of less than 4 causes pain to a patient. The pentosan polysulfate of the present invention is an active ingredient of a medicament, and can also function as a pH adjuster in an injectable formulation. The pentosan polysulfate of the present invention can be used for foods, medicaments, and any other compositions whose pH must be maintained in the range of pH 4 to pH 6 from the viewpoint of stabilization and prevention of degradation.

When a composition, such as an aqueous solution, contains the pentosan polysulfate of the present invention as a pH buffer agent, the concentration of pentosan polysulfate is preferably 10 to 500 mg/mL, and more preferably 50 to 300 mg/mL.

Method for Producing Pentosan Polysulfate

The pentosan polysulfate of the present invention can be obtained, for example, by a method for producing pentosan polysulfate, the method comprising Step I of obtaining an acidic xylooligosaccharide from a plant-derived raw material, and Step II of obtaining pentosan polysulfate from the acidic xylooligosaccharide; and further comprising a deacetylation step. In this method, Step I includes a step of depolymerizing a plant-derived raw material. Since the method comprises the step of depolymerizing a plant-derived raw material and the sulfation step in this order, the method can efficiently produce pentosan polysulfate. The method for producing pentosan polysulfate may further include a deacetylation step. By including a deacetylation step, the method can produce a pentosan polysulfate having a low acetyl group content.

Plant-Derived Raw Material

The acidic xylooligosaccharide can be obtained by depolymerizing a plant-derived raw material. Examples of plant-derived raw materials include wood-derived raw materials, seed-derived raw materials, grain-derived raw materials, fruit-derived raw materials, and the like. Further, examples of plant-derived raw materials that can be used include cottons such as cotton linter and cotton lint; herbaceous plants such as kenaf, hemp, ramie, and rice straw; and the like. As the plant-derived raw material, the above-mentioned raw materials derived from various sources may also be used in combination.

Among these, wood-derived raw materials are preferably used as the plant-derived raw material. Examples of usable wood-derived raw materials include wood raw materials such as softwoods and hardwoods. The wood-derived raw material is preferably at least one selected from softwoods and hardwoods; and hardwoods are more preferably used. The wood-derived raw material may be a mixture of softwood and hardwood. A bark may also be used as the wood-derived raw material.

Examples of hardwoods include beech, *Eucalyptus globulus, Eucalyptus grandis, Eucalyptus urograndis, Eucalyptus pellita, Eucalyptus braciana, Acacia mearnsii*, and the like. Examples of softwoods include Japanese cedar, Japanese cypress, pine, hiba, Japanese hemlock, and the like.

The wood-derived raw material preferably has a specific gravity of 450 kg/m$^3$ or more and 700 kg/m$^3$ or less, and more preferably 500 kg/m$^3$ or more and 650 kg/m$^3$ or less. When the wood-derived raw material has a specific gravity within the above-described range, the efficiency of producing acidic xylooligosaccharide can be further enhanced.

The wood-derived raw material is preferably wood chips obtained by crushing one or more of the above-mentioned woods. When wood chips are used as a plant-derived raw material, the depolymerization of a plant-derived raw material can be efficiently performed, and the efficiency of producing acidic xylooligosaccharide can be enhanced.

Step I
Depolymerization Step

Step I includes a step of depolymerizing a plant-derived raw material. In the step of depolymerizing a plant-derived raw material, the plant-derived raw material is chemically and/or physically decomposed to produce an acidic xylooligosaccharide. Examples of the chemical and/or physical decomposition step include a heat treatment step, an alkali treatment step, an acid treatment step, an enzyme treatment step, an ionic liquid treatment step, a catalytic treatment step, and the like. Among these steps, the depolymerization step is preferably a heat treatment step or an enzyme treatment step; and is more preferably a heat treatment step. The heat treatment step may be a heating and pressurizing step.

The depolymerization step is preferably performed under non-alkaline conditions (at pH 9 or less, and preferably pH 8 or less).

The heat treatment step is a step of heating a plant-derived raw material in the presence of a solution. Since the plant-derived raw material is hydrolyzed in such a heat treatment step, the heat treatment step is sometimes referred to as a hydrolysis treatment step or a pre-hydrolysis treatment step. The solution used in the heat treatment step is preferably water. The ratio (mass ratio) of water to the plant-derived raw material is preferably in the range of 1:1 to 1:10. When the ratio of water to the plant-derived raw material is set within the above-described range, the hydrolysis reaction can be efficiently performed. The water used in the heat treatment step may be water added separately from the plant-derived raw material; or a part of the water may be water originally contained in the plant-derived raw material.

In the heat treatment step, other chemicals may also be added, in addition to the plant-derived raw material and water. Examples of such other chemicals include alkalis, acids, and chelating agents. Further, chemicals that directly or indirectly assist the depolymerization of polysaccharides, such as scale inhibitors, pitch control agents, and ionic liquids, may also be added.

The heat treatment step is a step of heating a plant-derived raw material in the presence of water. The heating temperature (liquid temperature) in this step is preferably 30° C. or higher, more preferably 50° C. or higher, even more preferably 75° C. or higher, still even more preferably 90° C. or higher, particularly preferably 100° C. or higher, and most preferably 120° C. or higher. On the other hand, the heating temperature (liquid temperature) is preferably 300° C. or lower, more preferably 250° C. or lower, and even more preferably 200° C. or lower.

The treatment time in the heat treatment step can be determined, as appropriate, according to the treatment temperature. The treatment time is, for example, preferably 5 minutes or more, more preferably 10 minutes or more, and even more preferably 20 minutes or more. The P factor expressed by the following formula is a product of the heat treatment temperature and the heat treatment time. It is preferable to adjust the P factor within a preferred range.

$$P = \int_{t_0}^{t} \frac{k_{H1(T)}}{K_{100° C.}} \cdot dt = \int_{t_0}^{t} \text{Exp} \cdot \left(40.48 - \frac{15106}{T}\right) \cdot dt$$

In the above formula, P represents a P factor, T represents an absolute temperature (° C.+273.5), t represents the heat treatment time, and $K_{H1(T)}/K_{100° C.}$ represents the relative rate of hydrolysis of glycosidic bonds.

In the heat treatment step, the P factor is preferably set at 200 or more, more preferably 250 or more, and even more preferably 300 or more. On the other hand, the P factor is preferably 1000 or less. In the heat treatment step, the P factor is adjusted as appropriate so that the average degree of polymerization and the molecular weight of acidic xylooligosaccharide can be within desired ranges, whereby the molecular weight of the obtained pentosan polysulfate can be adjusted.

In the heat treatment step, the solution containing a plant-derived raw material preferably has a pH of 9 or less, more preferably pH 8 or less, and even more preferably pH 7 or less. That is, the heat treatment step is preferably performed under non-alkaline conditions. The pH values described above refer to the pH of the solution before the heat treatment.

In the heat treatment step, a raw material-derived acid may be dissociated, and acid hydrolysis may proceed at least partially. Examples of plant raw material-derived acids include organic acids, such as acetic acid and formic acid. In this case, the pH of the solution containing a plant-derived raw material is further decreased after the acid hydrolysis.

The method for producing pentosan polysulfate preferably comprises a heat treatment step as the first step. This can enhance the efficiency of producing acidic xylooligosaccharide, and further enhance the efficiency of producing pentosan polysulfate. When the method includes a heat treatment step as the first step, the number of steps required to produce acidic xylooligosaccharide can be significantly reduced, as compared with the conventional methods. By including a heat treatment under non-alkaline conditions as the first step, the method can efficiently produce acidic xylooligosaccharide with suppressed coloration, because the acidic xylooligosaccharide is not substituted with hexenuronic acid.

The depolymerization step is preferably a heat treatment step; however, it may be a step other than the heat treatment step. For example, when the depolymerization step is an enzyme treatment step, the depolymerization step includes a step of mixing a plant-derived raw material with an enzyme. Examples of usable enzymes include hemicellulase and the like. Specific examples include commercially available enzyme preparations, such as Cellulosin HC100 (trade name, manufactured by HBI Enzymes Inc.), Cellulosin TP25 (trade name, manufactured by HBI Enzymes Inc.), Cellulosin HC (trade name, manufactured by HBI Enzymes Inc.), Cartazyme (trade name, manufactured by Clariant AG), Ecopulp (trade name, manufactured by Rohm Enzyme GmbH), Sumizyme (trade name, manufactured by Shin Nihon Chemicals Corporation), Pulpzyme (manufactured by Novo Nordisk), and Multifect 720 (Genencor); and xylanase produced by microorganisms belonging to genus *Trichoderma*, genus *Thermomyces*, genus *Aureobasidium*, genus *Streptomyces*, genus *Aspergillus*, genus *Clostridium*, genus *Bacillus*, genus *Thermotoga*, genus *Thermoascus*, genus *Cardoceram*, genus *Thermomonospora*, or the like.

In the enzyme treatment step, an enzyme is added to a solution prepared by mixing a plant-derived raw material with water. The temperature of the solution during this treatment is preferably 10° C. or higher and 90° C. or lower, and more preferably 30° C. or higher and 60° C. or lower. The temperature of the solution is preferably a temperature close to the optimal temperature of the enzyme used. The pH of the solution is also preferably adjusted to a range in which the activity of the enzyme is enhanced. For example, the pH of the solution is preferably adjusted to a pH of 3 or more and a pH of 10 or less.

When the depolymerization step is an alkali treatment step or an acid treatment step, the depolymerization step comprises a step of mixing a plant-derived raw material with an alkaline solution or an acid solution. In the alkali treatment step, sodium hydroxide or potassium hydroxide is preferably added. In the acid treatment step, hydrochloric acid, sulfuric acid, acetic acid, or the like is preferably added. In such cases as well, heating or pressurization may be carried out, as appropriate.

When the depolymerization step is at least one selected from an enzyme treatment step, an alkali treatment step, and an acid treatment step, the production method may further comprise, after the treatment step, a squeezing step, an extraction step, a heating step, a filtration step, a separation step, a purification step, a concentration step, a desalination step, or the like. The method may further comprise a molecular weight reducing step performed after the treatment step. Examples of other steps include the steps described in JP2003-183303A, the contents of which are incorporated herein by reference.

Filtration Step

Step I may further comprise a filtration step performed after the depolymerization step described above. In the filtration step, the reaction mixture is separated into solids of the plant-derived raw material, and a solution other than the solids. More specifically, when Step I includes a filtration step performed after the depolymerization step, the reaction product is separated into solids, which are used as a pulp raw material, and a filtrate. The solids used as a pulp raw material are subjected to a digestion step or the like as a post-step, to provide a cellulose raw material (dissolving pulp).

The recovered filtrate can be separated into a gas layer and a liquid layer. Since the gas layer contains a large amount of furfurals, furfurals can be isolated by collecting these furfurals from the gas layer. On the other hand, the liquid layer contains a large amount of hemicellulose including acidic xylooligosaccharide and neutral xylooligosaccharide. In the step described below, the acidic xylooligosaccharide contained in this liquid layer can be separated and purified.

Separation and Purification Step

Step I may further comprise a separation and purification step performed after the depolymerization step. When Step I comprises the filtration step described above, a separation and purification step is preferably provided after the filtration step.

Step I may include a separation and purification step immediately after the depolymerization step. However, Step I preferably includes a filtration step performed after the depolymerization step; and includes a step of separating acidic xylooligosaccharide from the obtained filtrate, and purifying the neutral xylooligosaccharide. The filtration step may be provided as a part of the separation and purification step; or may be provided as one step that is independent from the separation and purification step. The separation and purification step is a step of separating and purifying acidic xylooligosaccharide. Since the filtrate obtained in the filtration step contains various saccharides, such as neutral xylooligosaccharide, in addition to acidic xylooligosaccharide, the separation and purification step is also a step of removing such xylooligosaccharides other than acidic xylooligosaccharide.

In the separation and purification step, for example, ion exchange chromatography, affinity chromatography, gel filtration, ion exchange treatment, NF membrane treatment, UF membrane treatment, RO membrane treatment, activated carbon treatment, or like methods are preferably used. In the separation and purification step, it is also preferable to perform the above methods in combination. In particular, when ion exchange chromatography is performed in the separation and purification, acidic xylooligosaccharide can be selectively separated and purified. In ion exchange chromatography, acidic xylooligosaccharide is adsorbed; accordingly, acidic xylooligosaccharide can be mainly obtained from the sugar liquid (filtrate). More specifically, sugar liquid is first treated with a strong cation exchange resin to remove metal ions from the sugar liquid. Subsequently, using a strong anion exchange resin, sulfate ions or the like are removed from the sugar liquid. The resulting sugar liquid is treated with a weak anion exchange resin to adsorb acidic xylooligosaccharide on the resin. An acidic xylooligosaccharide solution with fewer impurities can be obtained by eluting the acidic oligosaccharide adsorbed on the resin with a low-concentration salt (e.g., NaCl, $CaCl_2$), KCl, or $MgCl_2$).

Concentration Step

Step I may further comprise a concentration step. The concentration step is preferably provided, for example, after the filtration step, and before the separation and purification step. When Step I includes such a concentration step, the separation and purification step can be more efficiently performed, thus increasing the efficiency of producing pentosan polysulfate.

Examples of the concentration step include a membrane treatment step using an F membrane, an ultrafiltration membrane, a reverse osmosis membrane, or the like; a concentration step using evaporation etc.; and the like.

In the concentration step, the solution is preferably concentrated, so that the acidic xylooligosaccharide content is 10% or more and 80% or less, and more preferably 20% or more and 60% or less, based on the total mass of the concentrate.

Dehydration Step

In Step I, the acidic xylooligosaccharide may be obtained in the form of an acidic xylooligosaccharide solution; or may be subjected to a dehydration step, and thereby obtained in the form of an acidic xylooligosaccharide concentrate or an acidic xylooligosaccharide powder. When an acidic xylooligosaccharide powder is to be produced, the production method preferably further comprises a powdering step performed after the separation and purification step. When a dehydration step is included in the present invention, sulfation in the sulfation step described below can be performed more efficiently.

In the powdering step, the acidic xylooligosaccharide solution obtained in the separation and purification step is treated, for example, using a spray dryer, a freeze-drying machine, a hot-air drying machine, or a water-soluble organic solvent, to thereby obtain an acidic xylooligosaccharide powder.

Step II
Sulfation Step

The acidic xylooligosaccharide obtained in Step I is sulfated in Step II to thereby obtain pentosan polysulfate. That is, Step II comprises a sulfation step.

The average degree of polymerization of the acidic xylooligosaccharide to be subjected to sulfation is preferably adjusted, as appropriate, according to the molecular weight of pentosan polysulfate to be obtained as a final product.

The average degree of polymerization of the acidic xylooligosaccharides can be calculated by dividing the total sugar amount of the acidic xylooligosaccharide by the amount of reducing sugar. In calculation of the total sugar amount, first, an acidic xylooligosaccharide solution is maintained at 50° C. and centrifuged at 15000 rpm for 15 minutes. Thereafter, the total sugar amount of the supernatant is quantified by the phenol-sulfuric acid method ("*Kangento no Teiryo-Ho* (Method of Quantifying Reducing Sugar)"; published by Gakkai Shuppan Center). The calibration curve to be used in the quantification is produced using D-xylose (Wako Pure Chemical Industries, Ltd.). The amount of reducing sugar is quantified by the Somogyi-Nelson method ("*Kangento no Teiryo-Ho* (Method of Quantifying Reducing Sugar)"; published by Gakkai Shuppan Center). The calibration curve to be used in this quantification is also produced using D-xylose (Wako Pure Chemical Industries, Ltd.).

In the sulfation step, sulfuric acid or a sulfuric acid derivative is added to the acidic xylooligosaccharide solution to sulfate acidic xylooligosaccharide. Examples of sulfuric acid derivatives include sulfur trioxide pyridine complex, chlorosulfonic acid, and the like. In this step, the concentration of the acidic xylooligosaccharide solution is preferably 0.1 mass % or more and 20 mass % or less, and sulfuric acid is preferably added to the acidic xylooligosaccharide solution having such a concentration in an amount of 0.1 mass % or more and 50 mass % or less. The acidic xylooligosaccharide solution after addition of sulfuric acid preferably has a pH of 1 or more and 9 or less.

Post-Sulfation Purification Step

Step II may further comprise a post-sulfation purification step performed after the sulfation. When Step II includes such a post-sulfation purification step, a high-purity pentosan polysulfate can be obtained.

In the post-sulfation purification step, for example, centrifugation, membrane filtration, dialysis, water-soluble organic solvent treatment, activated carbon treatment, or like method is preferably used. Among these, water-soluble organic solvent treatment and activated carbon treatment are preferably used, because sulfonated pentosan polysulfate can be selectively separated and purified.

Powdering Step

In Step II, sulfated pentosan polysulfate may be obtained in the form of a pentosan polysulfate solution; or may be subjected to a powdering step, and thereby obtained in the form of a pentosan polysulfate powder. When a pentosan polysulfate powder is to be produced, the Step II preferably further includes a powdering step performed after the post-sulfation purification step.

In the powdering step, the pentosan polysulfate solution obtained in the post-sulfation purification step can be treated, for example, using a spray dryer, a freeze-drying machine, a hot-air drying machine, a water-soluble organic solvent, or the like, to thereby obtain a pentosan polysulfate powder.

Pentosan polysulfate is obtained by performing Step II described above. The pentosan polysulfate thus obtained preferably has a sulfur content of 10 mass % or more to 20 mass % or less, based on the total mass of the pentosan polysulfate. The sulfur content of pentosan polysulfate can be measured by the oxygen flask combustion method of the General Tests of the Japanese Pharmacopoeia.

Deacetylation Step

In the production of pentosan polysulfate, deacetylation is preferably performed. The deacetylation step is preferably performed at any stage after the depolymerization step. The deacetylation step can reduce the acetyl group content of pentosan polysulfate. Specifically, the deacetylation step is a step of adding a base to a solution containing a substance obtained from a plant-derived raw material, such as acidic xylooligosaccharide (also herein referred to as a "solution containing acidic xylooligosaccharide or the like"), so as to adjust the solution to pH 11 or more. In the deacetylation step, the solution obtained after the depolymerization, the filtrate obtained by the filtration step, the solution containing acidic xylooligosaccharide after the separation and purification step and before the sulfation step, the solution containing acidic xylooligosaccharide after the sulfation step (pentosan polysulfate), or the like may be adjusted to a pH of 11 or more. Among these solutions, when the solution containing acidic xylooligosaccharide after the separation and purification step and before the sulfation step is adjusted to pH 11 or more, a pentosan polysulfate having stable quality and a reduced acetyl group content can be obtained, and the sites where acetyl groups were bound can also be sulfated. Therefore, the sulfation efficiency, and thus the efficiency of producing pentosan polysulfate, can be increased. When the solution containing xylooligosaccharide obtained after the sulfation step (pentosan polysulfate) is adjusted to pH 11 or more, the purification step can be performed more efficiently. The solution containing acidic xylooligosaccharide or the like is preferably an aqueous solution. The solution containing acidic xylooligosaccharide may also be referred to herein as the acidic xylooligosaccharide solution.

The pH applied in the deacetylation step is preferably pH 11 to 14, and more preferably pH 12 to 13. The solution to be subjected to the deacetylation step is preferably maintained at pH 11 or more for 0.5 hours or more, more preferably at pH 11 or more for 1.0 hour or more, even more preferably at pH 11 or more for 2.0 hours or more, and particularly preferably at pH 11 or more for 3.0 hours or more. In particular, when the pH is less than 12, the solution is preferably maintained for 1.0 hour or more. Particularly preferred conditions may be, for example, conditions in which the solution is maintained at pH 12 to 13 for 3 hours or more.

While the solution is maintained in the above-described pH range, the solution is preferably stirred. The temperature applied while the solution is maintained in the above-described pH range is not particularly limited, but is preferably room temperature.

In the deacetylation step, a base may be added to a solution to be subjected to the deacetylation step (a solution containing acidic xylooligosaccharide or the like). The base to be added is not particularly limited, as long as the desired pH can be achieved. The base is preferably sodium hydroxide.

The deacetylation step may comprise a pH adjustment step of adjusting, to less than pH 11, the pH of a solution that has a pH of 11 or more, which results from the addition of a base after being maintained at the above-described pH. In the pH adjustment step, the solution may be adjusted to, for example, pH 9 or less, pH 8 or less, pH 7 or less, pH 6 or less, pH 5 or less, or pH 4 or less. The adjustment may be performed by adding an acid. Examples of usable acids include hydrochloric acid.

The deacetylation step preferably comprises a desalting step performed after the pH adjustment step. Desalting can be performed, for example, using a dialysis membrane or an NF membrane.

The deacetylation step may further comprise a step of powdering the obtained product for the subsequent treatment.

Other Steps

Molecular Weight Adjustment Step

The method for producing pentosane polysulfate may further comprise a molecular weight adjustment step between Step I and Step II. When the method for producing pentosan polysulfate includes a deacetylation step, the molecular weight adjustment step may be performed before or after the deacetylation step. In the molecular weight adjustment step, the molecular weight of the acidic xylooligosaccharide obtained in Step I is adjusted. For example, in the molecular weight adjustment step, the molecular weight of the acidic xylooligosaccharide can be reduced.

In the molecular weight adjustment step, a pentosan polysulfate having a weight average molecular weight of 1000 or more and 5000 or less can be obtained by performing, for example, acid treatment, alkali treatment, enzyme treatment, NF membrane treatment, UF membrane treatment, RO membrane treatment, gel filtration treatment, activated carbon treatment, ion exchange treatment, electrodialysis treatment, or the like. It is also possible to use a method of selectively collecting pentosan polysulfate having a desired weight average molecular weight by performing a membrane treatment or the like in the molecular weight adjustment step.

Post-Molecular-Weight-Adjustment Separation and Purification Step

The method for producing pentosan polysulfate may further comprise a post-molecular-weight-adjustment separation and purification step performed after the molecular weight adjustment step. Examples of the post-molecular-weight-adjustment separation and purification step may include gel filtration, ion exchange treatment, NF membrane treatment, UF membrane treatment, RO membrane treatment, electrodialysis treatment, activated carbon treatment, water-soluble organic solvent treatment, chromatographic treatment, and the like. When the production method includes such a post-molecular-weight-adjustment separation and purification step, acidic xylooligosaccharide having a desired molecular weight obtained in the molecular weight adjustment step can be selectively collected, and pentosan polysulfate having a narrow molecular weight distribution can be efficiently obtained.

EXAMPLES

The features of the present invention are described below more specifically with reference to Production Examples. The materials, amounts used, proportions, treatment content, treatment procedures, and the like described in the following Production Examples can be appropriately changed to the extent that such changes do not depart from the spirit of the present invention. Accordingly, the scope of the present invention should not be construed as being limited by the following specific examples.

Production of Acidic Xylooligosaccharide (1)

Fifty parts by mass of water was added to 10 parts by mass of wood chips (hardwood), and a heat treatment was performed at 165° C. for 3 hours. The resulting mixture was then subjected to solid-liquid separation using a Screw Press (manufactured by Shinryo Seisakusho: 250×1000 SPH-EN), and the filtrate was recovered. The filtrate was filtered through a bag filter with a micron rate of 1 μm (manufactured by ISP Filters). After 5 parts by mass of activated carbon (PM-SX; manufactured by Mikura Kasei Kabushiki Kaisha) was added to treat the filtrate at 50° C. for 2 hours, the resulting mixture, including the activated carbon, was further filtered through a ceramic filter with a micron rate of 0.2 μm (manufactured by Nihon Pall Co., Ltd.) to recover a clear filtrate. After the clear filtrate was concentrated 20-fold with a reverse osmosis membrane (NTR-7450; manufactured by Nitto Denko Corporation) to obtain a concentrated sugar liquid, the concentrated sugar liquid was passed at SV 1.5 through a 4-bed 4-tower type ion exchange resin system consisting of a strong cationic resin (PK-218; manufactured by Mitsubishi Chemical Corporation), a weak anionic resin (WA30; manufactured by Mitsubishi. Chemical Corporation), a strong cationic resin (PK-218; manufactured by Mitsubishi Chemical Corporation), and a weak anionic resin (WA30; manufactured by Mitsubishi Chemical Corporation). Acidic xylooligosaccharide was thereby adsorbed on the weak anionic resin of the second and fourth towers. A 50 nV sodium chloride aqueous solution was then passed through the second and fourth towers at SV 1.5 to recover an acidic xylooligosaccharide solution. Sodium hydroxide was added to the obtained acidic xylooligosaccharide solution to achieve a pH of 13, and the resulting mixture was stirred at room temperature for 3 hours for deacetylation. After hydrochloric acid was added to the resulting solution to achieve a pH of less than 5 and desalting was performed using a dialysis membrane (Spectra/Por 7, CE membrane, MWCO 100-500; manufactured by Spectrum), the resulting mixture was powdered using a freeze-drying machine (manufactured by EYELA).

Production of Neutral Xylooligosaccharide

Fifty parts by mass of water was added to 10 parts by mass of wood chips (hardwood), and a heat treatment was performed at 165° C. for 3 hours. The resulting mixture was then subjected to solid-liquid separation using a Screw Press (manufactured by Shinryo Seisakusho: 250×1000 SPH-EN), and the filtrate was recovered. The filtrate was further filtered through a bag filter with a micron rate of 1 μm (manufactured by ISP Filters). After 5 parts by mass of activated carbon (PM-SX; manufactured by Mikura Kasei Kabushiki Kaisha) was added to treat the filtrate at 50° C. for 2 hours, the resulting mixture, including the activated carbon, was further filtered through a ceramic filter with a micron rate of 0.2 μm (manufactured by Nihon Pall Co., Ltd.) to recover a clear filtrate. After the clear filtrate was concentrated 20-fold with a reverse osmosis membrane (NTR-7450; manufactured by Nitto Denko Corporation) to obtain a concentrated sugar liquid, the concentrated sugar liquid was passed at SV 1.5 through a 4-bed 4-tower type ion exchange resin system consisting of a strong cationic resin (PK-218; manufactured by Mitsubishi Chemical Corporation), a weak anionic resin (WA30; manufactured by Mitsubishi Chemical Corporation), a strong cationic resin (PK-218; manufactured by Mitsubishi Chemical Corporation), and a weak anionic resin (WA30; manufactured by Mitsubishi Chemical Corporation) to thereby recover a neutral xylooligosaccharide solution. Sodium hydroxide was added to the obtained neutral xylooligosaccharide solution to achieve a pH of 13, and the resulting mixture was stirred at room temperature for 3 hours for deacetylation. After hydrochloric acid was added to the obtained solution to achieve a pH of less than 5, and the obtained salt was removed using a dialysis membrane (Spectra/Por 7, CE membrane, MWCO 100-500; manufactured by Spectrum), the resulting mixture was powdered using a freeze-drying machine (manufactured by EYELA).

Production of Pentosan Polysulfate Sodium

Comparative Example 1

25 mL of N,N-dimethylformamide, 12.4 g of sulfur trioxide pyridine complex, and 1.5 g of the neutral xylooligosaccharide powder produced by the method described above were placed in a 100-mL separable flask, and a reaction was allowed to proceed at 40° C. for 3 hours. After cooling, the obtained reaction mixture was added dropwise to 500 mL of ethanol. The generated precipitate was collected by filtration, and 30 mL of water was added to dissolve the precipitate therein. A sodium hydroxide solution was added to the obtained solution to achieve a pH of 10. The resulting solution was added dropwise to 500 mL of ethanol, and the obtained precipitate was then collected by filtration. Thereafter, 30 mL of water was added to dissolve the precipitate therein; and activated carbon was added to the solution and stirred, followed by filtration. The filtrate was concentrated using an evaporator, and powdered using a freeze-drying machine (manufactured by EYELA).

Comparative Example 2

Pentosan polysulfate sodium was obtained in the same manner as in Comparative Example 1, except that a mixture of 1.125 g of neutral xylooligosaccharide powder and 0.375 g of acidic xylooligosaccharide (1) was used in place of 1.5 g of the neutral xylooligosaccharide powder of Comparative Example 1.

Example 1

Pentosan polysulfate sodium was obtained in the same manner as in Comparative Example 1, except that a mixture of 0.375 g of neutral xylooligosaccharide powder and 1.125 g of acidic xylooligosaccharide (1) was used in place of 1.5 g of the neutral xylooligosaccharide powder of Comparative Example 1.

Example 2

Pentosan polysulfate sodium was obtained in the same manner as in Comparative Example 1, except that 1.5 g of acidic xylooligosaccharide (1) was used in place of 1.5 g of the neutral xylooligosaccharide powder of Comparative Example 1.

Physical Property Values

The uronic acid content, average molecular weight, and sulfur content of pentosan polysulfates of Examples 1 and 2, and Comparative Examples 1 and 2 were measured as follows.

Uronic Acid Content

About 10 mg of pentosan polysulfate sodium obtained in each of the Examples and Comparative Examples was weighed out and dissolved in distilled water to make the volume exactly 25 mL. 1 mL of each solution was placed in a test tube. While the solution was cooled in ice water, 5 mL of a solution of 0.025M sodium tetraborate in sulfuric acid was added and mixed, and the resulting mixture was heated in a water bath for 10 minutes. Immediately after heating, the resulting mixture was ice-cooled, and 0.2 mL of a carbazole reagent was added and mixed. The resulting mixture was heated in a water bath for 15 minutes, and then allowed to cool to obtain a sample solution. Separately, glucuronic acid standard stock solutions in a concentration of 10 to 100 μg/mL were prepared and subjected to the same procedure as above to obtain standard solutions. 1 mL of distilled water was also subjected to the same procedure, and the resulting liquid was used as a control. Absorbance at a wavelength of 530 nm was measured. Calibration curves were prepared from the absorbance of the standard solutions, and the amount of glucuronic acid (g) in the Examples and Comparative Examples was determined. The uronic acid content (mass %) was calculated according to the following formula. When the quantitative value was negative, it was regarded as 0%.

Uronic acid content (mass %)=Amount of glucuronic acid (μg)/(Weighed amount of pentosan polysulfate sodium×1/25)/10

Sulfur Content

The sulfur content was measured by the oxygen flask combustion method described in the Japanese Pharmacopoeia.

Average Molecular Weight

The weight average molecular weight (Mw) of the pentosan polysulfate of the present invention can be determined by GPC (gel permeation chromatography). A YMC-Pack Diol-300 and YMC-Pack Diol-60 (both manufactured by YMC) connected to each other can be used as a GPC column. GPC was performed, for example, under the following conditions.

Eluent: 25 mM potassium dihydrogen phosphate/25 mM dipotassium hydrogen phosphate/50 mM potassium chloride
Flow rate: 0.7 mL/min
Measurement temperature: 40° C.
Detector: refractive index detector Inhibitory Activity to Inhibit the Binding Between FGF-2 and Heparan Sulfate 10 mg of pentosan polysulfate of each of the Examples and Comparative Examples was dissolved in 10 mL of saline. The resulting solutions were mixed with biotinylated heparan sulfate, and stirred at 37° C. for 15 minutes. As a blank, a sample obtained by mixing only saline with biotinylated heparan sulfate was also prepared. These solutions were added to an FGF-2 immobilized plate, and the plate was stirred at 37° C. for 15 minutes. After the solutions were removed and wells of the plate were washed with 0.1% Tween 20/PBS three times, an avidin-HRP solution was added, and the plate was stirred at 37° C. for 15 minutes.

After the solution was removed and the wells of the plate were washed with 0.1% Tween 20/PBS three times, a substrate for HRP was added to allow color to develop at room temperature for about 5 minutes. After a reaction-stopping solution was added and stirred, the absorbance at a wavelength of 450 nm (A450 nm) was measured. The inhibition rate was calculated by the following formula.

Inhibition rate (%)=($A$450 nm(blank)−$A$450 nm(pentosan polysulfate))/$A$450 nm(blank)

The biotinylated heparan sulfate, FGF-2 immobilized plate, avidin-HRP solution, and HRP substrate used were those included in an Heparan Degrading Enzyme Assay Kit (Takara Bio Inc.). Tween 20, PBS, and the reaction-stopping solution used were those included in a Wash and Stop Solution for ELISA without Sulfuric Acid (Takara Bio Inc.).

Table 1 and FIG. 1 show the results.

TABLE 1

|  | Comparative Example 1 | Comparative Example 2 | Example 1 | Example 2 |
|---|---|---|---|---|
| Uronic acid content (mass %) | 0.00 | 1.64 | 7.94 | 12.61 |
| Average molecular weight | 2053 | 2168 | 2487 | 2781 |
| Sulfur content (mass %) | 15.34 | 15.09 | 14.33 | 13.28 |
| FGF inhibition rate (%) | 81.8 | 90.8 | 94.5 | 95.4 |

The results in Table 1 and FIG. 1 show that pentosan polysulfate sodium having a uronic acid content of 7.0 mass % to 15.0 mass % exhibits a high FGF inhibition rate.

Production of Acidic Xylooligosaccharide (2)

Fifty parts by mass of water was added to 10 parts by mass of wood chips (hardwood), and a heat treatment was performed at 165° C. for 3 hours. The resulting mixture was then subjected to solid-liquid separation using a Screw Press (manufactured by Shinryo Seisakusho: 250×1000 SPH-EN), and the filtrate was recovered. The filtrate was further filtered through a bag filter with a micron rate of 1 μm (manufactured by ISP Filters). After 5 parts by mass of activated carbon (PM-SX; manufactured by Mikura Kasei. Kabushiki Kaisha) was added to treat the filtrate at 50° C. for 2 hours, the resulting mixture, including the activated carbon, was further filtered through a ceramic filter with a micron rate of 0.2 m (manufactured by Nihon Pall Co., Ltd.) to recover a clear filtrate. After the clear filtrate was concentrated 20-fold with a reverse osmosis membrane (NTR-7450; manufactured by Nitto Denko Corporation) to obtain a concentrated sugar liquid, the concentrated sugar liquid was passed at SV 1.5 through a 4-bed 4-tower type ion exchange resin system consisting of a strong cationic resin (PK-218; manufactured by Mitsubishi Chemical Corporation), a weak anionic resin (WA30; manufactured by Mitsubishi Chemical Corporation), a strong cationic resin (PK-218; manufactured by Mitsubishi Chemical Corporation), and a weak anionic resin (WA30; manufactured by Mitsubishi Chemical Corporation). Acidic xylooligosaccharide was thereby adsorbed on the weak anionic resin of the second and fourth towers. A 50 mM sodium chloride aqueous solution was then passed through the second and fourth towers at SV 1.5 to recover an acidic xylooligosaccharide solution. The obtained acidic xylooligosaccharide solution was powdered using a freeze-drying machine (manufactured by EYELA).

Production of Acidic Xylooligosaccharide (3)

An acidic xylooligosaccharide (3) was obtained in the same manner as in the production of the acidic xylooligosaccharide (1), except that deacetylation was performed at pH 11 for 1 hour.

Production of Acidic Xylooligosaccharide (4)

An acidic xylooligosaccharide (4) was obtained in the same manner as in the production of the acidic xylooligosaccharide (1), except that deacetylation was performed at pH 11 for 2 hours.

Production of Acidic Xylooligosaccharide (5)

An acidic xylooligosaccharide (5) was obtained in the same manner as in the production of the acidic xylooligosaccharide (1), except that deacetylation was performed at pH 12 for 1 hour.

Production of Pentosan Polysulfate Sodium 2

Comparative Example 3

Pentosan polysulfate sodium was obtained in the same manner as in Comparative Example 1, except that 1.5 g of acidic xylooligosaccharide powder (2) was used in place of 1.5 g of the neutral xylooligosaccharide powder of Comparative Example 1.

Examples 3 to 5

Pentosan polysulfate sodium of each of Examples 3 to 5 was obtained in the same manner as in Comparative Example 1, except that 1.5 g of acidic xylooligosaccharides (3) to (5) was used in place of 1.5 g of the neutral xylooligosaccharide powder of Comparative Example 1.

Physical Properties and Inhibitory Activity to Inhibit the Binding Between FGF-2 and Heparan Sulfate The uronic acid content and the average molecular weight of the pentosan polysulfates of Examples 3 to 5 and Comparative Example 3 were determined in the same manner as in Example 1. The acetyl group content of the pentosan polysulfates of Examples 2 to 5 and Comparative Example 3 was determined in the following manner.

35 mg of sodium 3-(trimethylsilyl)propionate-2,2,3,3-d4 (produced by Isotec Corporation) was dissolved in heavy water (produced by Kanto Kagaku). Using a 25-mL measuring flask, the solution was diluted to prepare an internal standard solution. The pentosan polysulfate sodium obtained in each of the Examples and Comparative Examples was weighed (30 mg) and dissolved in 1 mL of the internal standard solution to prepare a solution for NMR measurement. The obtained solution was transferred to an NMR sample tube (produced by Kanto Kagaku), and $^1$H-NM measurement was performed using FT-NMR (JNM-LA400; produced by JEOL Ltd.). The acetyl group content was calculated from the integral ratio of the peak for trimethylsilyl group of the internal standard substance and the peak for acetyl group of pentosan polysulfate sodium.

Figure 2:
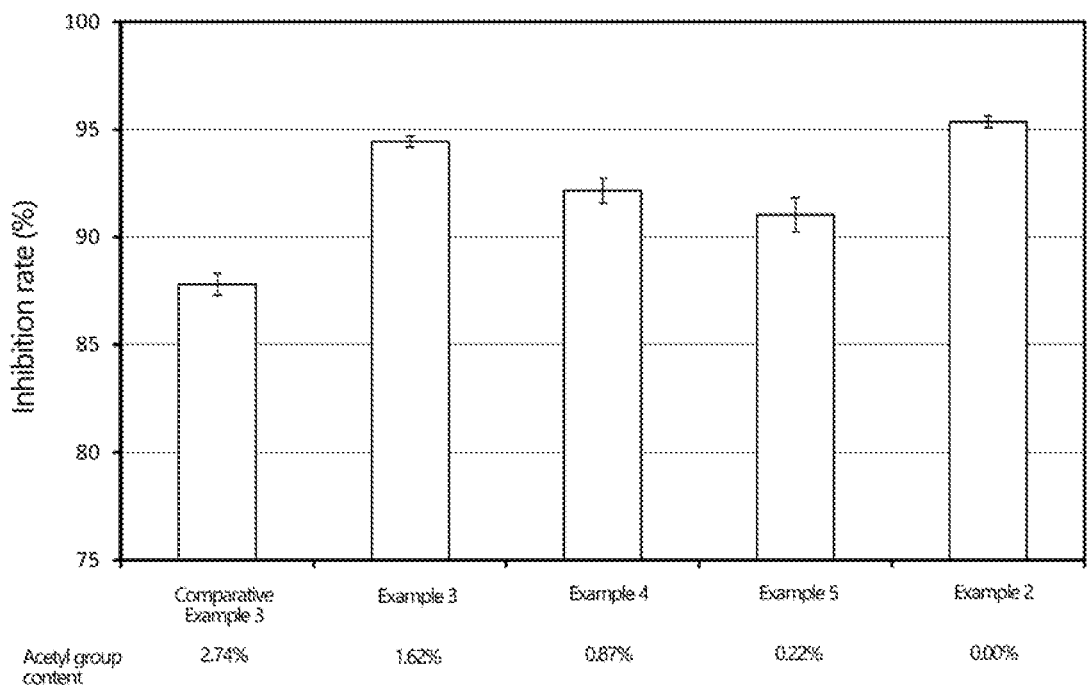
FIG. 2 is a graph showing the effect of the acetyl group content of pentosan polysulfate on inhibitory activity to inhibit the binding between FGF-2 and heparan sulfate.

The uronic acid content, the average molecular weight, and the inhibitory activity to inhibit the binding between FGF-2 and heparan sulfate, of the pentosan polysulfates of Examples 2 to 5 and Comparative Example 3 were determined in the same manner as in Example 1. Table 2 and FIG. 2 show the results.

TABLE 2

|  | Comparative Example 3 | Example 3 | Example 4 | Example 5 | Example 2 |
|---|---|---|---|---|---|
| Average molecular weight | 2211 | 2356 | 2325 | 2129 | 2781 |
| Uronic acid content (mass %) | 11.03 | 11.40 | 11.42 | 10.83 | 12.61 |
| Acetyl group content (mass %) | 2.74 | 1.62 | 0.87 | 0.22 | 0.00 |
| FGF inhibition rate (%) | 87.8 | 94.4 | 92.2 | 91.0 | 95.4 |

Storage Stability

The pentosan polysulfate sodium of each of Examples 2 and 4 and Comparative Example 3 was dissolved in purified water to a concentration of 100 mg/mL, and the resulting solutions were sealed in screw vials. The properties of each solution after storage at 40° C. for week and 2 weeks were visually confirmed.

TABLE 3

|  |  | Example 2 | Example 4 | Comparative Example 3 |
|---|---|---|---|---|
| Acetyl group content (mass %) |  | 0.00% | 0.87% | 2.74% |
| Properties of the solution | Initial | Colorless transparent | Colorless transparent | Colorless transparent |
|  | 40° C., 1 week | Colorless transparent | Colorless transparent | Slightly yellow transparent |
|  | 40° C., 2 weeks | Slightly yellow transparent | Slightly yellow transparent | Yellow transparent |

The results in Table 2 and FIG. 2 show that any pentosan polysulfate sodium having an acetyl group content of less than 2.0% had an FGF inhibition rate of more than 90%, thus exhibiting a high inhibition rate. Table 3 shows that when aqueous pentosan polysulfate sodium solutions having a low acetyl group content are stored at room temperature or higher, coloring hardly occurs, and the solutions are highly stable.

pH Buffering Action of Pentosan Polysulfate 100 mg of pentosan polysulfate obtained in each of Examples 1 and 2 and Comparative Examples 1 and 2 was dissolved in water to make the total volume exactly 100 ml. This solution was adjusted to pH 10 using a 0.01N sodium hydroxide aqueous solution (produced by Kanto Kagaku) with an automatic titrator (produced by DKK Toa Corporation). Titration was then performed using a 0.01N aqueous hydrochloric acid solution (produced by Kanto Kagaku) with the automatic titrator. The amount of 0.1N aqueous hydrochloric acid solution required to adjust the pH of the pentosan polysulfate solution from pH 6 to pH 4 was calculated.

Figure 3:
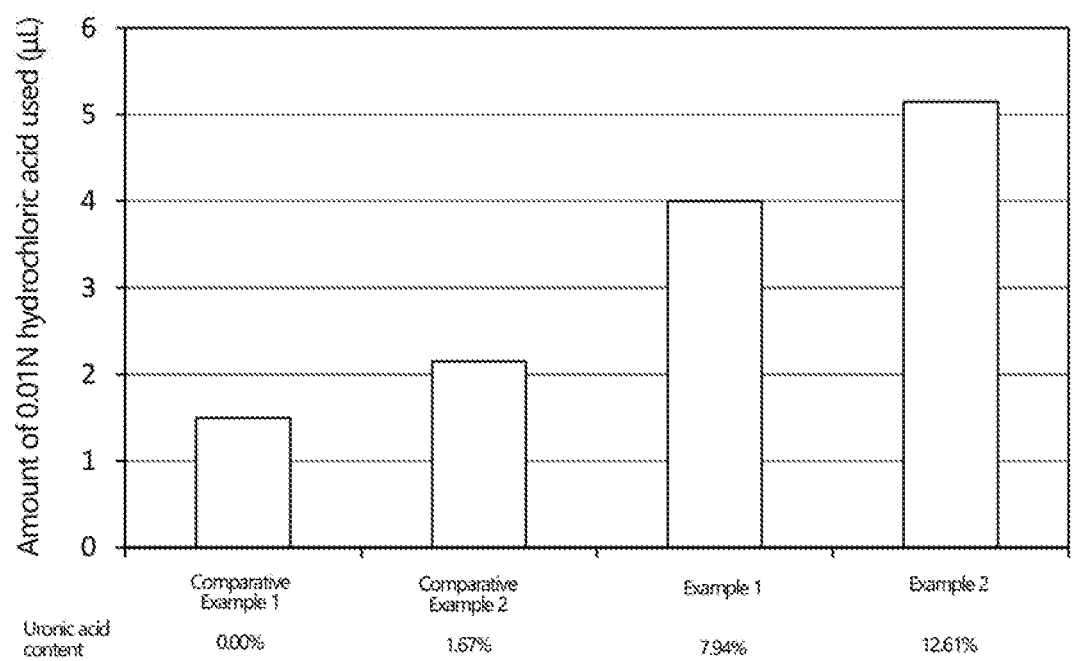
FIG. 3 is a graph showing the relationship between the uronic acid content of pentosan polysulfate, and the amount (mL) of a 0.01N hydrochloric acid aqueous solution required to adjust the pH from pH 6 to pH 4 in the titration of the 100 mg/100 mL pentosan polysulfate solution.

FIG. 3 shows the results.

The results of FIG. 3 clearly show that the pentosan polysulfates of the Examples exhibit high buffering action to maintain the pH in the range of pH 4 to pH 6.

The invention claimed is:

1. A pentosan polysulfate having a uronic acid content of 7.0 mass % to 15.0 mass %, and an acetyl group content of 0 mass % to 2.0 mass %;
   a pharmaceutically acceptable salt thereof; or
   a pharmaceutically acceptable solvate of the pentosan polysulfate or of the pharmaceutically acceptable salt thereof.

2. The pentosan polysulfate according to claim 1, wherein the pentosan polysulfate has a uronic acid content of 7.5 mass % to 13.0 mass %;
   a pharmaceutically acceptable salt thereof; or
   a pharmaceutically acceptable solvate of the pentosan polysulfate or of the pharmaceutically acceptable salt thereof.

3. The pentosan polysulfate according to claim 1, wherein the pentosan polysulfate has a weight average molecular weight of 5000 or less;
   a pharmaceutically acceptable salt thereof; or
   a pharmaceutically acceptable solvate of the pentosan polysulfate or of the pharmaceutically acceptable salt thereof.

4. The pentosan polysulfate according to claim 3, wherein the pentosan polysulfate has an acetyl group content of 0 to 0.3 mass %;
   a pharmaceutically acceptable salt thereof; or
   a pharmaceutically acceptable solvate of the pentosan polysulfate or of the pharmaceutically acceptable salt thereof.

5. The pentosan polysulfate according to claim 1, wherein the pentosan polysulfate has a structure represented by Formula II:

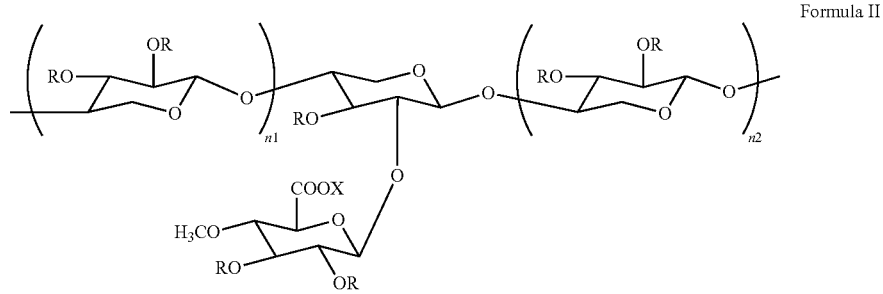

Formula II wherein R each independently represents a hydrogen atom, —COCH$_3$, or —SO$_3$X$^1$, and at least one R in the molecule is —SO$_3$X$^1$, wherein X$^1$ represents a hydrogen atom or a monovalent or divalent metal;

X represents a hydrogen atom or a monovalent or divalent metal; and n1 and n2 each independently represent an integer of 0 or more and 30 or less, and at least one of n1 and n2 is an integer of 1 or more;

a pharmaceutically acceptable salt thereof; or a pharmaceutically acceptable solvate of the pentosan polysulfate or of the pharmaceutically acceptable salt thereof.

6. The pentosan polysulfate according to claim 5, wherein each R independently represents a hydrogen atom or —SO$_3$X$^1$;

a pharmaceutically acceptable salt thereof; or a pharmaceutically acceptable solvate of the pentosan polysulfate or of the pharmaceutically acceptable salt thereof.

7. The pentosan polysulfate according to claim 5, wherein X$^1$ represents sodium;

a pharmaceutically acceptable salt thereof; or a pharmaceutically acceptable solvate of the pentosan polysulfate or of the pharmaceutically acceptable salt thereof.

8. A medicament comprising the pentosan polysulfate according to claim 1;

a pharmaceutically acceptable salt thereof; or a pharmaceutically acceptable solvate of the pentosan polysulfate or of the pharmaceutically acceptable salt thereof.

9. A method of treating a disease caused by abnormal enhancement of FGF-2 function, the method comprising:

administering the medicament according to claim 8 to the subject in need thereof.

10. The method according to claim 9, wherein the disease caused by abnormal enhancement of FGF-2 function is cancer, autoimmune disease, allergic disease, inflammatory disease, cardiac dysplasia, vascular dysplasia, or skeletal dysplasia.

11. The method according to claim 9, wherein the disease caused by abnormal enhancement of FGF-2 function is cystitis or arthritis.

12. The medicament according to claim 8, which is an injectable formulation.

13. A pH buffer agent comprising the pentosan polysulfate according claim 1;

a pharmaceutically acceptable salt thereof; or a pharmaceutically acceptable solvate of the pentosan polysulfate or of the pharmaceutically acceptable salt thereof.

14. The pentosan polysulfate according to claim 6, wherein X$^1$ represents sodium;

a pharmaceutically acceptable salt thereof; or a pharmaceutically acceptable solvate of the pentosan polysulfate or of the pharmaceutically acceptable salt thereof.

15. The pentosan polysulfate according to claim 1, wherein the pentosan polysulfate has an acetyl group content of 0 mass % to 1.62 mass %;

a pharmaceutically acceptable salt thereof; or a pharmaceutically acceptable solvate of the pentosan polysulfate or of the pharmaceutically acceptable salt thereof.

* * * * *